US00PP35444P2

(12) United States Plant Patent
Martin et al.

(10) Patent No.: US PP35,444 P2
(45) Date of Patent: Oct. 31, 2023

(54) AVOCADO TREE NAMED 'BL516'

(50) Latin Name: ***Persea americana* Mill**
Varietal Denomination: BL516

(71) Applicant: The Regents of the University of California, Oakland, CA (US)

(72) Inventors: Gray E. Martin, Fallbrook, CA (US); Berthold O. Bergh, Riverside, CA (US); David Stottlemyer, Oakland, CA (US); Eric D. Focht, Moreno, CA (US); Mary Lu Arpaia, Visalia, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/803,098

(22) Filed: Feb. 4, 2022

(51) Int. Cl.
*A01H 5/08* (2018.01)
*A01H 6/52* (2018.01)

(52) U.S. Cl.
USPC ..... Plt./200

(58) Field of Classification Search
USPC ..... Plt./156, 200
See application file for complete search history.

(56) References Cited

PUBLICATIONS

Ying. 2009. Selection of Highly Informative microsatellite markers to identify pollen donors in 'Haas' Avocado Orchards. Plant Mol. Biol Reg. 27: 374-380. (Year: 2009).*
University of California Agriculture & Natural Resources: Avocado information website citation for 'BL516' (Marvel). http://ucavo.ucr.edu/avocadovarieties/UnreleasedVarieties/BL516.html. 1 page. (Year: 2022).*
Ashworth, et al., "Microsatellite Markers in Avocado (*Persea americana Mill.*): Genealogical Relationships Among Cultivated Avocado Genotypes," Journal of Heredity 2003:94(5) pp. 407-415.

* cited by examiner

*Primary Examiner* — Karen M Redden
(74) *Attorney, Agent, or Firm* — Kilpatrick Townsend & Stockton LLP

(57) ABSTRACT

'BL516' is a new and distinct variety of *Persea americana* tree. The variety exhibits an upright growth habit with strongly drooping branches; and forms pyriform, slightly obovate or occasionally rhomboidal shaped generally black-skinned fruit when ripe that lack shoulders and is well distributed around the tree. The fruit is comparable in size to that of the 'Hass' variety and matures slightly later then the fruit of the 'Hass' variety. 'BL516' fruit has yellow-green flesh of excellent eating quality that is free of obvious fibers. The 'BL516' variety forms leaves in greater quantity than the 'Hass' variety and displays moderate resistance to the *Persea* mite.

3 Drawing Sheets

Genus and species: The avocado cultivar of this invention is botanically identified as *Persea americana* Mill.

Variety denomination: The variety denomination is 'BL516'.

BACKGROUND OF THE INVENTION

The invention relates to a new and distinct variety of avocado tree named 'BL516'. The new avocado variety originated from a breeding program at the University of California, Riverside, for the development of new avocado varieties.

The seed that produced 'BL516' was collected in 1983 from open pollinated 'Gwen' (U.S. Plant Pat. No. 5,298) avocado plants. The exact pollen parent is unknown. Seeds were planted in a test planting area in Ventura County, Calif. to produce avocado seedlings in the spring of 1985. A single plant of 'BL516' was selected with initial evaluation occurring in May 1991. 'BL516' was first top-worked by grafting onto *Persea americana* seedlings in the spring of 1991 in Irvine, Calif. The first fruit from the trees was tested in June 1994. This initial and subsequent asexual propagation confirmed that the new variety is stable and the progeny remain true to type.

BRIEF SUMMARY OF THE INVENTION

'BL516' exhibits the following combination of characteristics compared to other known varieties:

(a) 'BL516' has an upright growth habit with strongly-drooping branches.

(b) 'BL516' has pyriform, slightly obovate or occasionally rhomboidal-shaped, generally black-skinned fruit when ripe that lacks shoulders and is well distributed around the tree. In general, fruit is comparable in size and matures later than fruit of the 'Hass' variety. The fruit has yellow-green flesh of excellent eating quality that is free of obvious fibers.

(c) 'BL516' forms leaves in greater quantity than the 'Hass' variety.

(d) 'BL516' displays moderate resistance to the *Persea* mite.

'BL516' can be distinguished from all previously known avocado varieties including 'Hass' (U.S. Plant Pat. No. 35), 'Gwen' (U.S. Plant Pat. No. 5,298), 'Sir Prize' (U.S. Plant Pat. No. 9,709), 'Lamb Hass' (U.S. Plant Pat. No. 9,573), 'N4(-)5' (U.S. Plant Pat. No. 14,238), '3-29-5' (U.S. Plant Pat. No. 14,239), and 'BL 5-552' (U.S. Plant Pat. No. 33,534) in view of its distinctive combination of characteristics.

'BL516' is believed to be well-suited for the production of quality avocados under commercial growing conditions.

BRIEF DESCRIPTION OF THE PHOTOGRAPHS

DETAILED BOTANICAL DESCRIPTION

Figure 1:
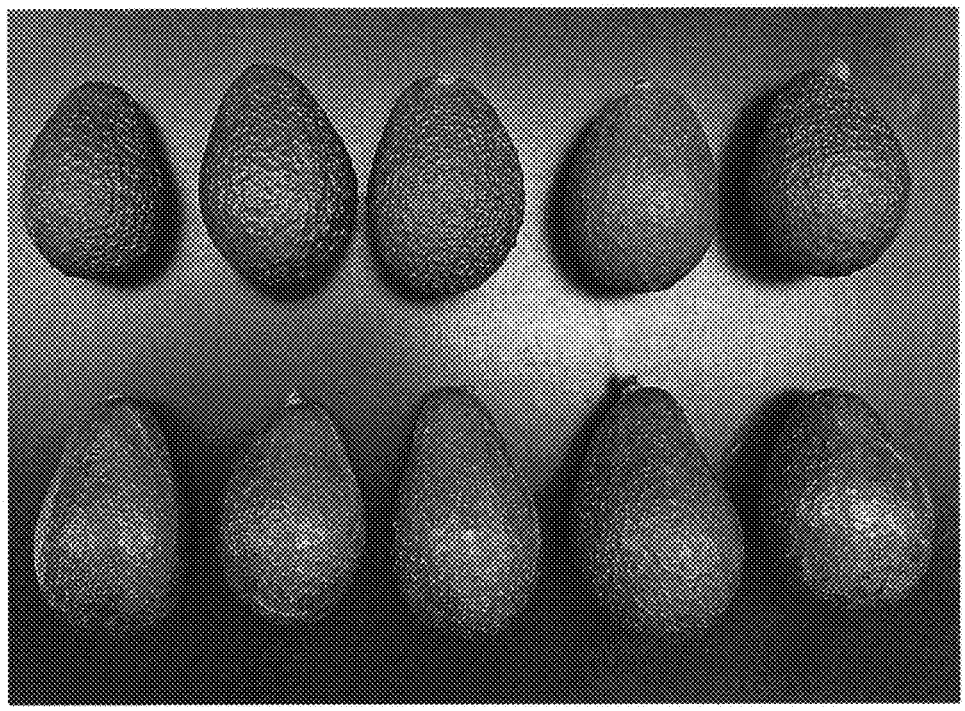
FIG. 1 illustrates typical unripe 'BL516' fruit (bottom row) compared to unripe 'Hass' fruit (top row). All fruit were harvested in Irvine, Calif. in January 2022.
Figure 2:
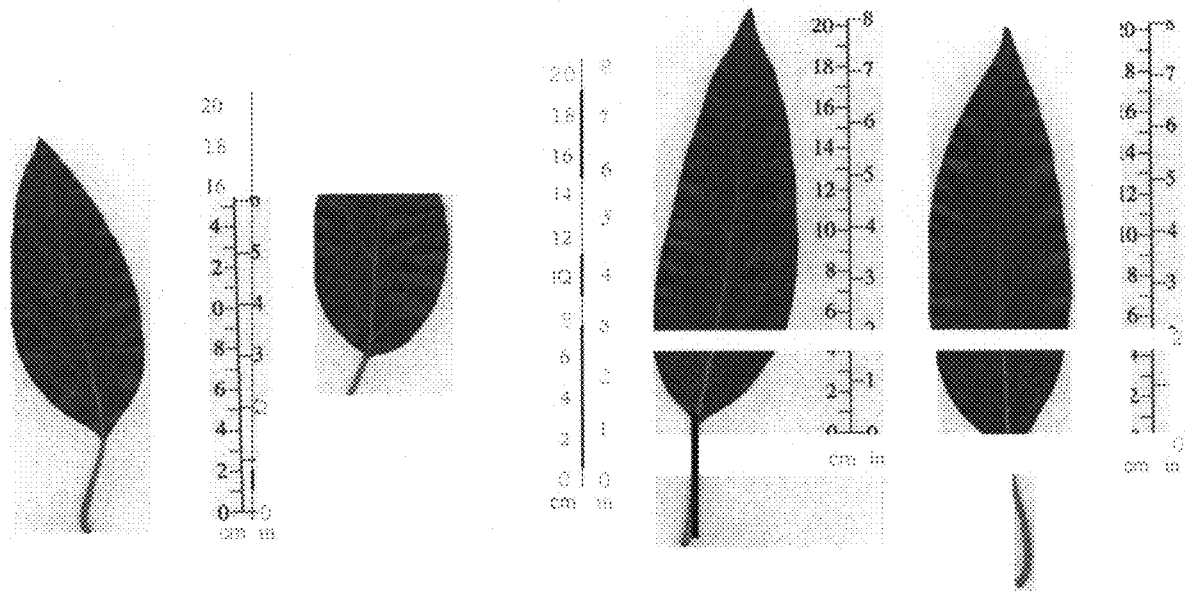
FIG. 2 illustrates four typical mature leaves of the 'BL516' variety. Leaves were collected from mature 'BL516' trees in the fall of 2014.
Figure 3:
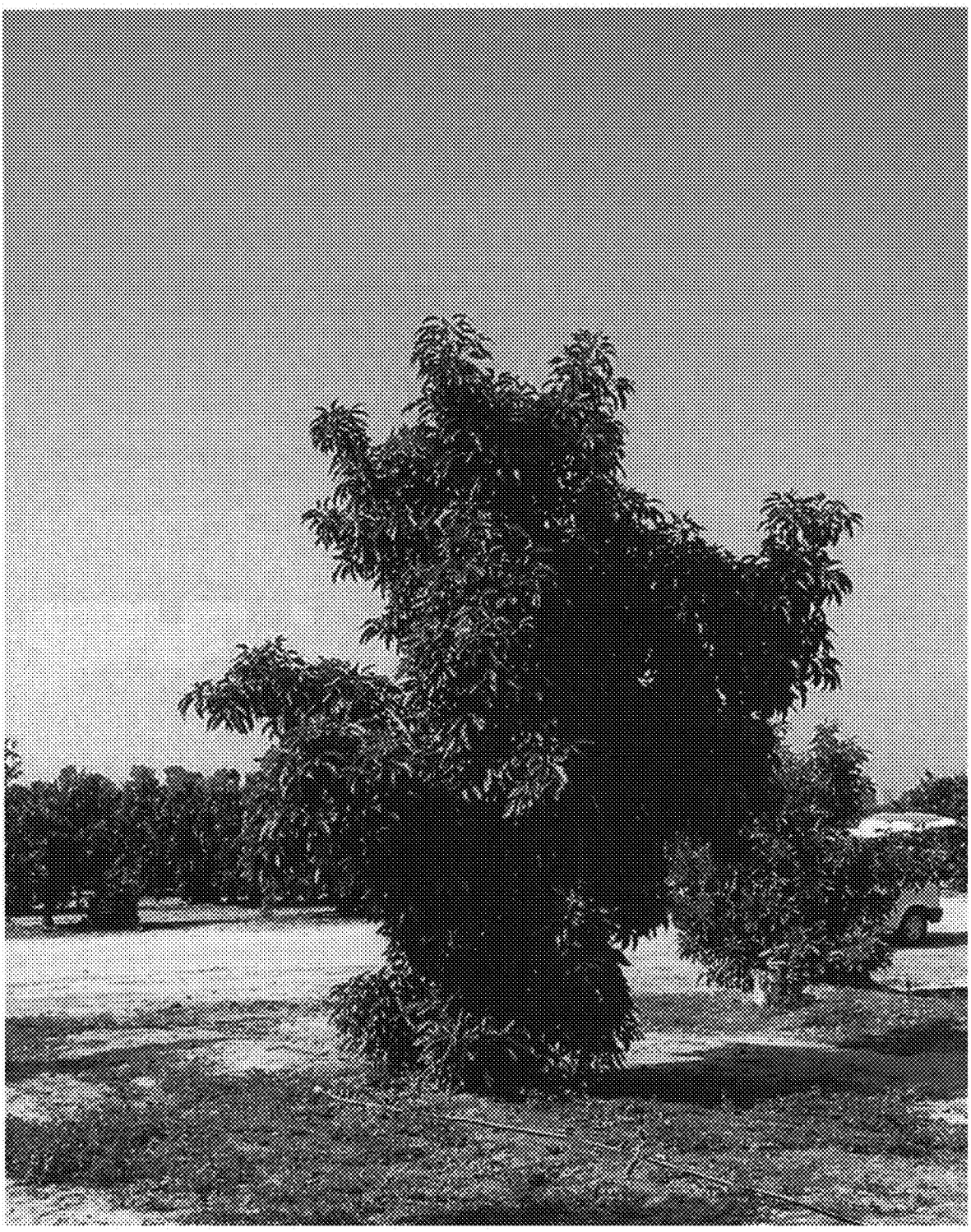
FIG. 3 illustrates a four-year-old top-worked tree of the 'BL516' variety growing in Irvine, Calif.

The following is a description of 'BL516' trees that were grown at experimental orchards in Irvine, Calif. unless otherwise indicated. The trees were approximately 2 to 17 years of age, and had been grafted on *Persea americana* seedling or clonal 'Dusa' rootstock. Where possible, comparison varieties were of approximately equivalent age. The comparative trees for the 'Gwen' variety, however, were mature and their exact age is unknown. Color information is designated with reference to The R.H.S. Colour Chart of the Royal Horticultural Society, London, England, 2001.

Tree:

*Growth habit.*—'BL516' is upright in growth habit with strongly-drooping branches compared to an upright habit with semi-drooping branches for the 'Gwen' and 'Lamb Hass' varieties; and upright and spreading habit with no drooping branches for variety 'N4(-)5'. Internode lengths on the shoot are mostly short, but occasionally intermediate, compared to mostly intermediate to short lengths for the 'Lamb Hass' variety, intermediate lengths for the 'Gwen' variety, and intermediate to long lengths for the 'N4(-)5' variety.

*Height.*—Averaging 4.5 m for fully mature trees, about 10-15-years old, which is similar to the 'N4(-)5' variety, compared to an average height of 4.4 m for the 'Hass' variety and 4.3 m for the '3-29-5' and 'Lamb Hass' varieties.

*Width.*—Averaging 3.3 m for fully mature trees, which is similar to the '3-29-5' variety, compared to an average width of 3.8 m for the 'N4(-)5' variety, 3.6 m for the 'Lamb Hass' variety, and 4.1 m for the 'Hass' variety.

*Canopy volume.*—A comparison of 'BL516' canopy volume to 'Hass' canopy volume is provided in Table 1. Volume was determined using a formula that includes tree height and the average canopy width taken at chest height from two trials, one in Irvine, Calif. and the other in Exeter, Calif. in the San Joaquin Valley. The trees were planted in 2013 on 'Dusa' clonal rootstock. Measurements (Table 1) were from mature trees, taken in Fall 2020. For the Irvine site, 'BL516' tree volume was approximately 45% of the canopy volume of Hass. The Exeter site provided similar results, in which the 'BL516' tree volume was again about 45% of that of Hass.

TABLE 1

A comparison of 'BL516' to 'Hass' trees 7 years after planting in terms of average canopy width, tree height and canopy volume.

| Site | Variety | Canopy width (m) | Tree Height (m) | Canopy Volume ($m^3$) |
|---|---|---|---|---|
| Irvine | BL516 | 3.46 b | 4.23 a | 27.19 b |
| | Hass | 5.08 a | 4.27 a | 60.62 a |
| Exeter | BL516 | 2.77 b | 3.09 b | 13.63 b |
| | Hass | 3.58 a | 4.47 a | 29.83 a |

Mean separation using Student-Newman-Keulstest at $P < 0.05$. The designations "a" and "b" shown for each comparison characteristic at each site indicate that the means are statistically different at the 95% confidence level.Two "a" value designations for a given comparison indicate th at the means are not statistically different at the 95% confidence level. Each site analyzed separately. Tree numbers for each site: Hass, 3 trees; BL516,15 trees.

Canopy width for individual trees was measured down the row and across the row and then averaged.

Canopy volume calculated using the following formula: (Height * (Average canopy width)$^2$) * 0.5236

Main stem:

*Bark.*—Substantially identical to that of the 'Hass', 'Gwen', 'N4(-)5', and '3-29-5' varieties. The new wood is smooth without corky lenticels. The old wood is corky in appearance as observed with most other avocado varieties and light brown or gray, RHS Greyed-Green Group 197D, in coloration.

*Trunk size.*—Trees average 49.1 cm in circumference, as measured at approximately 30 cm above the soil line, above the graft union and before major branching occurs, compared to an average circumference of 47.2 cm for the '3-29-5' variety, 57.8 cm for the 'N4(-)5' variety, 53.8 cm for the 'Hass' variety, and 51.7 cm for the 'Lamb Hass' variety.

Branch:

*Color.*—The color of a one-year-old branch is RHS Yellow Green 145A. The most recent fully-formed young shoot (flush) is also RHS Yellow Green 145A.

*Smoothness.*—The bark of a one-year-old branch is smooth.

*Lenticels.*—The lenticels of a one-year-old branch are conspicuous and are RHS Yellow Green 143A in color, while the lenticels of the most recent fully-formed flush are generally RHS Yellow Green 144A.

Young shoot (flush):

*Intensity of anthocyanin coloration.*—Strong, RHS Greyed Purple Group N186C; Underside is RHS Greyed Orange Group 175A. Young leaf surface is medium glossy.

*Young shoot color of lenticels.*—Not very conspicuous. Yellow to light green in color, generally RHS Yellow Green 144A. Lenticels are generally between 0.8 mm and 2.9 mm in length and are at a density of about 17 per $cm^2$. Young shoot main color is RHS Yellow Green Group N144A.

Mature leaf:

*Shape.*—Generally lanceolate to somewhat oval with an acute tip and an acute base. The shape is substantially the same as that of 'N4(-)5' and '3-29-5' varieties, compared to more oval to somewhat lanceolate for the 'Hass' variety, or more oblong lanceolate to lanceolate for the 'Gwen' variety. Leaf base is acute and leaf apex is mostly acute, which is substantially similar to 'Gwen' and 'N4(-)5' compared to the 'Hass' or '3-29-5' varieties, which have a more intermediate to acute apex. The leaf blade of 'BL516' does not twist along its entire length, nor does the apex of the leaf exhibit twisting.

*Bearing*.—Alternate.

*Attitude*.—Outwards and upwards attitude of leaf to branch, which is similar to the 'Lamb Hass' variety, compared to an upwards attitude for the 'N4(-)5' variety, and an upwards and outwards attitude for the 'Gwen' variety.

*Length*.—Approximately 18.2 cm compared to 19.9 cm for the 'Gwen' and 'Hass' varieties, 15.3 cm for the '3-29-5' variety, and 20.0 cm for the 'N4(-)5' variety.

*Width*.—Approximately 6.9 cm compared to 6.7 cm for the 'Gwen' variety, 7.8 cm for the 'Hass' and 'N4(-)5' varieties, and 6.4 cm for the '3-29-5' variety.

*Leaf weight*.—Approximately 2.78 grams compared to approximately 3.95 grams for the 'Hass' variety, 2.05 grams for the '3-29-5' variety, 2.65 grams for the 'N4(-)5' variety, and 2.30 grams for the 'Gwen' variety.

*Color*.—Near RHS Yellow-Green Group 146A on the upper surface and near RHS Yellow-Green Group 148D on the under surface.

*Texture*.—Pubescent when young and leathery when mature.

*Venation*.—Pinnate and near RHS Yellow-Green Group 145C in color. Venation on upper surface is level with the rest of leaf surface.

*Margin*.—Entire. Leaf undulation is very weak.

*Petiole*.—Generally 57.7 mm in length, and approximately 2.7 mm in diameter. Color of petiole is RHS Yellow-Green Group 153A or RHS Yellow Green Group N144A.

*Anise aroma*.—Absent.

Flower:

*Bud size*.—Approximately 3.6 mm in length and 2.1 mm in diameter.

*Bud shape*.—Ovate/oval initially, progressing to oval/lanceolate.

*Bud color*.—RHS Yellow-Green Group 150C.

*Opening*.—Belongs to flowering group "B". Opens as female in the afternoon of the first day and closes in the evening or early night to open as male the morning of the second day. Accordingly, it can be inter-planted with complementary flower types to possibly boost fruit set and yield by making pollen available at the appropriate time. Pollinators (e.g. European honey bees) can facilitate fruit set.

*Petals*.—Borne in two whorls of three perianth lobes. The petals are intact, pubescent, and possess margins that are not wavy or undulating. The petal coloration is near RHS Yellow-Green Group 154C.

*Stamen*.—There commonly are nine fertile stamens with each having four pollen chambers, two basal orange nectar glands, and three staminoidia. The anthers are tetrathecal.

*Pistil*.—The single pistil has one carpel with one ovule. The ovary is superior.

*Pedicel*.—Approximately 4.1 mm in length and 0.5 mm in diameter. The coloration is near RHS Yellow-Green Group 151B.

*Number of flowers on infloresence*.—Approximately 10 flowers per infloresence.

*Fragrance*.—Absent.

*Bloom*.—Bloom period in Irvine, Calif. varies with culture and environmental conditions. Based on observations over several years, 'BL516' typically blooms from February through May.

Fruit and Production Characteristics

Fruit:

*Length*.—Approximately 10.0 cm.

*Width*.—Approximately 6.7 cm.

*Weight*.—Approximately 219.9 grams. This is comparable to the 'Hass' variety, which averages 220.0 grams, but smaller than the '3-29-5' and 'Lamb Hass' varieties, which average 266.5 grams and 274.2 grams respectively for this comparison in Irvine, Calif.

*Shape*.—Generally pyriform or slightly obovate to occasionally rhomboidal with the fruit apex slightly asymmetric in position with a slightly depressed to flattened shape, and a diameter of 3.9 cm on average. The fruit base is depressed to somewhat flattened with a diameter of 5.8 cm on average. In comparison, the 'Hass' variety varies from ellipsoid to obovate, the 'Gwen' and 'N4(-)5' varieties are generally an inverted high spheroid, and the '3-29-5' variety is generally inverted high spheroid.

*Color of skin*.—Mature, hard fruit varies in a range including RHS Green Group 136A, RHS Greyed-Green Group N189A, RHS Green Group 135A, RHS Greyed Purple Group N186A and RHS Greyed Purple Group 187A. Mature, soft fruit varies in a range including RHS Greyed Purple Group N186A, RHS Greyed Purple Group N186B, RHS Greyed Purple Group N187A, and RHS Green Group 139A. Immature, hard fruit varies in a range including RHS Yellow Green Group 144A, RHS Yellow Green Group N144A, RHS Green Group 141B, RHS Green Group 143A, RHS Green Group N134A, RHS Green Group 141B, and RHS Green Group 135B. Lenticels are distinct from background color, much like the '3-29-5' variety.

*Texture of skin*.—Slightly pebbled.

*Presence of longitudinal ridges*.—Absent.

*Thickness of skin*.—Somewhat leathery in consistency, not corky or membranous. Skin thickness averages 1.2 mm compared to 1.6 mm for the 'Hass' variety, 1.8 mm for the '3-29-5' variety, and 1.5 mm for the 'Lamb Hass' variety.

*Adherence of skin to flesh*.—Minimal.

*Main color of flesh*.—RHS Yellow Group 11A or RHS Yellow Group 13B towards the center of the fruit and RHS Yellow Green Group N144B near the skin.

*Width of intensely colored area next to the skin*.—Approximately 2.8 mm.

*Conspicuousness of fibers in flesh*.—Inconspicuous.

*Fruit pedicel*.—Approximately 10.9 mm in diameter. Pedicel color is RHS Yellow Green 144A, RHS Yellow Green 145A or RHS Yellow Green 146D and generally has a wrinkled surface.

*Time of harvesting*.—'BL516' typically ripens later than the 'Hass' variety and is similar to the '3-29-5' variety in Southern California planting environments such as Irvine, Calif. The typical optimal harvest period in Irvine, Calif. for good storability and eating-quality fruit is approximately from April through July.

Seed:

*Length*.—Approximately 4.1 cm.

*Width*.—Approximately 3.4 cm.

*Weight*.—Approximately 31.2 grams. This is smaller than the 'Hass', '3-29-5', and 'Lamb Hass' varieties measured, which averaged 31.6 grams, 43.2 grams, and 35.1 grams respectively.

*Shape* (*in longitudinal section*).—Almost equally tending towards ellipsoid or broadly ovate compared to the 'N4(-)5' and 'Gwen' varieties, which are spheroid; the 'Hass' variety, which is variable but mostly ellipsoid; or the '3-29-5' variety, which is broadly obovate.

*Shape* (*in cross section*).—Generally circular.

*Color of seed coat* (*fresh*).—Ranges from RHS Greyed Orange Group 166A, RHS Greyed Purple Group 183A, RHS Greyed Purple Group 183B, RHS Greyed Orange Group 177A, RHS Greyed Purple Group 186C, to RHS Greyed Purple Group 187A.

*Cotyledon color*.—Generally ranges from RHS Orange White Group 159A and RHS Orange White Group 159B to Orange White Group 159C.

Productivity: Generally comparable to that of the 'Hass' variety, but with perhaps less precocity. Table 2 provides a comparison of cumulative fruit count, yield, average fruit size and alternate bearing index. Fruit is borne on the inner branches of the tree, however, and more protected from sun, wind or other weather damage. 'BL516' has lower alternate bearing tendency than the 'Hass' or 'Lamb Hass' varieties, similar to the '3-29-5' variety.

TABLE 2

A comparison of 'BL516' to 'Hass' trees 9 years after planting in terms of cumulative fruit count, yield (kg), average fruit size and alternate bearing index.

| Site | Variety | Cumulative Fruit Count | Cumulative Weight (kg) | Average fruit size (g) | Alternate Bearing Index |
|---|---|---|---|---|---|
| Irvine | BL516 | 610.5 a | 131.2 a | 213.5 a | 0.59 a |
| | Hass | 659.3 a | 144.9 a | 220.0 a | 0.76 a |

TABLE 2-continued

A comparison of 'BL516' to 'Hass' trees 9 years after planting in terms of cumulative fruit count, yield (kg), average fruit size and alternate bearing index.

| Site | Variety | Cumulative Fruit Count | Cumulative Weight (kg) | Average fruit size (g) | Alternate Bearing Index |
|---|---|---|---|---|---|
| Exeter | BL516 | 210.1 a | 29.7 a | 165.4 a | 0.33 b |
| | Hass | 389.0 a | 53.9 a | 138.6 a | 0.81 a |

Mean separation using Student-Newman-Keulstest at $P < 0.05$. The designations "a" and "b" shown for each comparison characteristic at each site indicates whether the means are statistically different at a 95% confidence level. Two "a" value designations for a given comparison indicate that the means are not statistically different at a 95% confidence level. Each site analyzed separately. Trees planted in 2013 on 'Dusa' clonal rootstock. Tree numbers for each site: Hass, 3 trees; BL516,15 trees. Alternate Bearing Index year-5 to year-10 were used to calculate I, based on the calculation of Hoblyn et al. (1936): $I = (1/n) \times [I''/y - y//(y + y)]$, where yi is the observed yield in an ordered series of size n, and _yi − yi − 1_ is the absolute difference between successive yields. Alternate bearing index calculated beginning with year 4.

Hardiness: Generally comparable to the 'Hass' variety (USDA hardiness zone 9-11). For comparative purposes, the '3-29-5' is considered to be more cold-tolerant whereas the 'Gwen' and 'N4(-)5' varieties are considered to be less cold-hardy.

Market Use

'BL516' avocados have excellent eating-quality and can compete favorably with the 'Hass' variety for both fresh retail and food service markets. The fruit exhibits post-harvest handling and storage traits that allow it to be treated in much the same manner as the 'Hass', '3-29-5', and 'Lamb Hass' commercial varieties.

The narrow, upright canopy makes the 'BL516' variety a candidate for high-density or hedge-row avocado plantings. Tree size and shape are also desirable qualities for backyard growers. 'BL516' thus also has retail nursery value.

The B flowering-type indicates that it can be a useful pollinizer for 'Hass', 'Reed', '3-29-5', 'Lamb Hass', and other flowering group A-type commercial varieties.

What is claimed:

1. A new and distinct variety of avocado tree named 'BL516', substantially as illustrated and described herein.

* * * * *